United States Patent [19]

Warriner

[11] Patent Number: Plant 7,096

[45] Date of Patent: Jan. 9, 1990

[54] ROSE PLANT JACBRO

[75] Inventor: William A. Warriner, Tustin, Calif.

[73] Assignee: Jackson & Perkins Company, Medford, Oreg.

[21] Appl. No.: 284,296

[22] Filed: Dec. 14, 1988

[51] Int. Cl.[4] ..... A01H 5/00

[52] U.S. Cl. ..... Plt./11

[58] Field of Search ..... Plt. 11, 16, 17

*Primary Examiner*—James R. Feyrer

*Attorney, Agent, or Firm*—Majestic, Parsons, Siebert & Hsue

[57] ABSTRACT

A rose variety of the hybrid tea class is provided that has a high production of large apricot and yellow blend flower color with good fragrance. The plant is large and vigorous.

1 Drawing Sheet

SUMMARY OF THE INVENTION

The present invention relates to a new and distinct variety of rose plant of the hybrid tea class, which was originated by me by crossing the variety Sunbright, U.S. Plant Pat. No. 4,438, with the variety Medallion, U.S. Plant Pat. No. 2997.

The primary objective of this breeding was to produce a new rose variety of the hybrid tea class having large blooms in the yellow-orange color range on a vigorous plant. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. An upright habit and grows to a height of five or more feet in California;
2. Considerable fragrance;
3. Apricot and yellow blend colored flower petals;
4. Medium number of prickles on stems;
5. Reddish new foliage; and
6. A free blooming habit and produces flowers in good quantity.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose variety, which has been denominated "Jacbro". Color terminology is in accordance with The Royal Horticultural Society Colour Chart except where an ordinary dictionary significant for the color is apparent.

Observations of the buds and flowers were made from specimens grown in a garden environment in November at Somis, Calif.

Flower

The blooming habit is continuous. The bud size is one and one-half to two inches when the petals start to unfurl. The bud form is long with a broad base. The bud color when sepals first divide is near Orange-Red Group 30B. When half blown, the upper side of petals is near Orange Group 26B. The lower side of petals is near Orange-Red Group 30C fading to Yellow-Orange Group 22A near petal base. The sepals have a color near Green Group 137D. The outside surface texture of the sepals is smooth and the inside surface is hairy. There are three normally appendaged sepals, and two unappendaged sepals with a hairy edge and glandular structure. The receptacle color is near Green Group 137D and has a funnel shape, small size and smooth surface. The peduncle is medium in length and has a glandular surface. Peduncle color is bronzy and the peduncle is stiff and erect.

Bloom

Bloom size is very large, with an average open size of four to four and one-half inches, borne singly. The stems are strong and medium in length. The form when first open is cupped and flat. All petals curl towards the end of bloom. Under normal conditions there are 25 to 30 petals. At the center of the flower, the upper side of the petals is near Orange Group No. 26B and the reverse side of the petals at the flower center are near Orange-Red Group 30C. The base of petals is near Yellow-Orange Group 22A. The major color is near Orange Group 26A. There are no variegations. The general tonality at the end of the first day shows no change in color. At the end of the third day, the color begins to pale slightly.

There is moderate fragrance. The petal texture is thin. The petal shape is deltoid and the form is moderately quilled. The arrangement is imbricated with few petaloids in the center. The blooms drop off cleanly, and last both on the plant and as a cut flower for a long time.

Reproductive Parts

The anthers are of medium size, of yellow color and arranged regularly around the styles. The filaments are yellow, the pollen is lemon yellow, the styles are red, and the stigmas are pale yellow.

Plant

The plant has very vigorous, upright growth of bush form.

Foliage

The foliage is medium size and normal in quantity. New foliage is reddish green in color and old foliage is near the Yellow-Green Group 147A. A normal mid-stem leave has five leaflets.

The leaflets have an oval pointed shape, are smooth textured, and have a serrated edge. The serration is single and small. Petiole rachis is green, and petiole underside is smooth, with occasional prickles. Stipules are medium and serrated. As the stems mature to the point of flowering, the rachis and leaflet midveins remain red while the leaf tissue has changed to green. The foliage is susceptible to mildew under normal growing conditions at Wasco and Irvine, Calif.

Wood

New wood is reddish colored with a smooth bark. Old wood is green with a smooth bark.

Prickles

There are an ordinary number of prickles on the main canes from the base and on the laterals from the main canes. The prickles are medium and angled downward. The prickles are red and green and red colored when young. There are no small prickles on the main stalks and a few brown colored small prickles on the laterals.

Parentage

The seed parent was of the variety Sunbright. The pollen parent was of the variety Medallion.

Classification

Botanical is rosa hybrid. Commercial is hybrid tea.

I claim:

1. A new and distinct variety of rose plant of the hybrid tea class substantially as herein shown and described, characterized particularly as to novelty by the large apricot and yellow blend flower color, with good fragrance, good bloom production and a large vigorous plant growth.

* * * * *

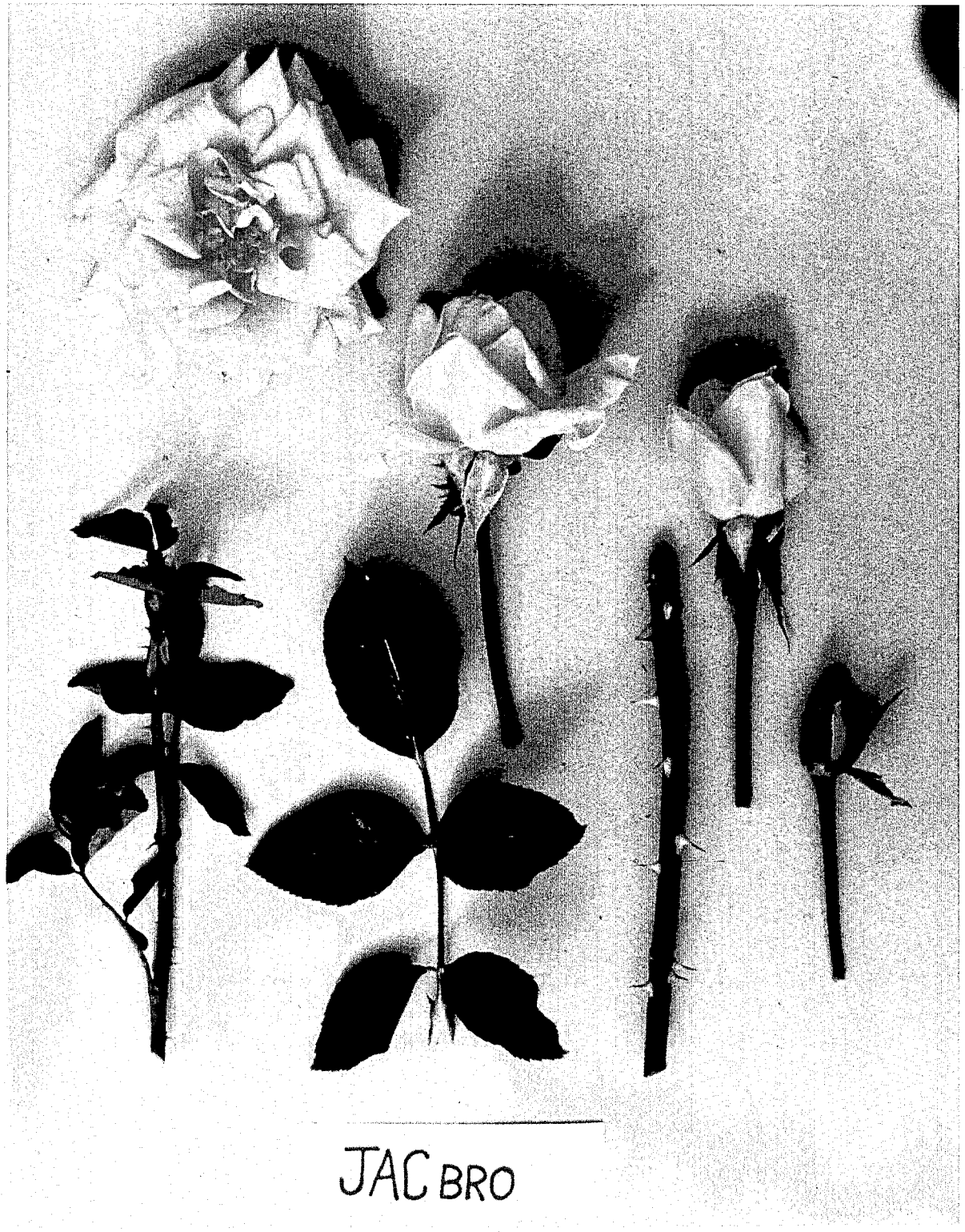
JAC BRO